(12) United States Patent
Yan et al.

(10) Patent No.: US 8,852,763 B2
(45) Date of Patent: *Oct. 7, 2014

(54) PERFLUOROPOLYETHER CONTAINING LUBRICANTS WITH MIXED END GROUPS

(75) Inventors: Xiaoping Yan, Pleasanton, CA (US); Michael Josesph Stirniman, Fremont, CA (US)

(73) Assignee: Seagate Technology LLC, Cupertino, CA (US)

( * ) Notice: Subject to any disclaimer, the term of this patent is extended or adjusted under 35 U.S.C. 154(b) by 99 days.

This patent is subject to a terminal disclaimer.

(21) Appl. No.: 13/455,222

(22) Filed: Apr. 25, 2012

(65) Prior Publication Data

US 2013/0288080 A1 Oct. 31, 2013

(51) Int. Cl.
*G11B 5/66* (2006.01)
*G11B 5/725* (2006.01)
*C07F 9/6593* (2006.01)

(52) U.S. Cl.
CPC ............ *G11B 5/725* (2013.01); *C07F 9/65815* (2013.01)
USPC ........... 428/835.8; 508/422; 508/582; 564/13

(58) Field of Classification Search
None
See application file for complete search history.

(56) References Cited

FOREIGN PATENT DOCUMENTS

| WO | WO 2009/066784 | 5/2009 |
|---|---|---|
| WO | WO 2009/122988 | 10/2009 |
| WO | WO 2010/027096 | 3/2010 |

OTHER PUBLICATIONS

English machine translation of JP 2000-260017, Japan, Sep. 2000.*

* cited by examiner

*Primary Examiner* — Holly Rickman
(74) *Attorney, Agent, or Firm* — Mueting, Raasch & Gebhardt, P.A.

(57) ABSTRACT

Compounds of formula I:

(I)

wherein X are independently $-(CH_2)_b-$, wherein b is 0 or an integer from 1 to 6; $R_f$ are independently $-CF_2O(CF_2CF_2O)_p(CF_2)_qCF_2-$, $-CF_2CF_2O(CF_2CF_2CF_2O)_rCF_2CF_2-$, or $-CF_2CF_2CF_2O(CF_2CF_2CF_2CF_2O)_sCF_2CF_2CF_2-$, or derivatives thereof, wherein p, q, r and s are independently integers so that $M_n$ of $R_f$ is about 150 to 4500; and Z are independently chosen from groups that comprise $-OH$, $-(OH)_2$, $-COOCH_3$, $-F$, $-CF_3$, or $-CF_2CF_3$, with the caveat that not all Z are the same.

17 Claims, 1 Drawing Sheet

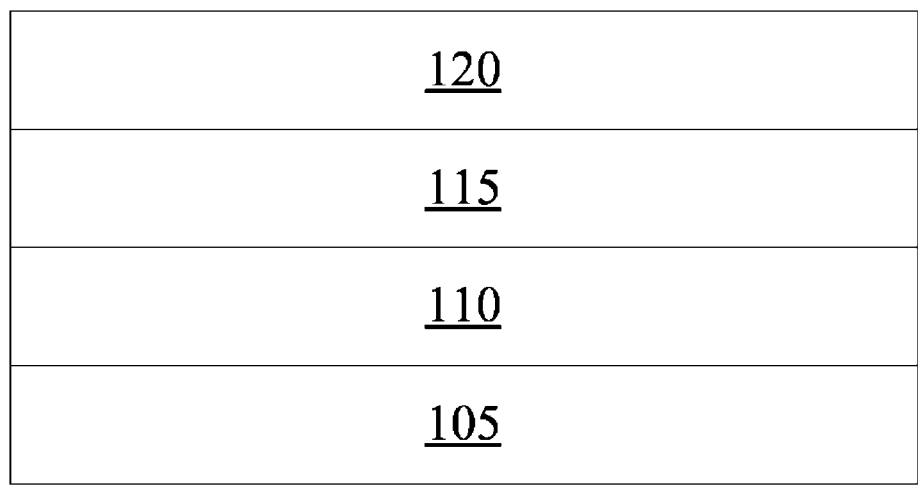

PERFLUOROPOLYETHER CONTAINING LUBRICANTS WITH MIXED END GROUPS

BACKGROUND

Magnetic storage media are moved relative to a magnetic head in order to read and write information to and from the magnetic disc. The magnetic storage media, or disc typically includes a substrate, an underlayer, a magnetic layer, an overcoat layer, and a lubricant layer. In order to maximize the capacity of a magnetic disc, the magnetic head desirably flies as close as possible to the magnetic disc. The lubricant layer is designed to reduce the wear and tear that such low flight heights can cause. As the fly height, or head media spacing (referred to as "HMS") decreases, new and more effective lubricants become necessary.

SUMMARY

Disclosed herein are compounds of formula I:

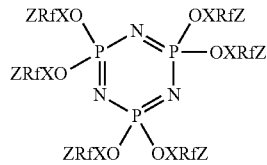

(I)

wherein X are independently $-(CH_2)_b-$, wherein b is 0 or an integer from 1 to 6; $R_f$ are independently $-CF_2O(CF_2CF_2O)_p(CF_2O)_qCF_2-$, $-CF_2CF_2O(CF_2CF_2CF_2O)_rCF_2CF_2-$, or $-CF_2CF_2CF_2O(CF_2CF_2CF_2CF_2O)_sCF_2CF_2CF_2-$, or their derivatives wherein p, q, r and s are independently integers so that $M_n$ of $R_f$ is about 150 to 4500; and Z are independently chosen from groups that comprise $-OH$, $-(OH)_2$, $-F$, $-CF_3$, or $-CF_2CF_3$, with the caveat that not all Z are the same.

Disclosed herein are magnetic stacks that includes: a substrate, a magnetic layer on the substrate, the magnetic layer configured to store data; a protective overcoat on the magnetic layer; and a lubricant layer on the protective overcoat, the lubricant layer including at least one compound of formula I:

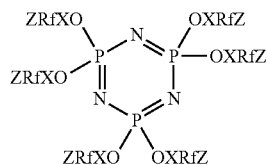

(I)

wherein X are independently $-(CH_2)_b-$, wherein b is 0 or an integer from 1 to 6; $R_f$ are independently $-CF_2O(CF_2CF_2O)_p(CF_2O)_qCF_2-$, $-CF_2CF_2O(CF_2CF_2CF_2O)_rCF_2CF_2-$, $-CF_2CF_2CF_2O(CF_2CF_2CF_2CF_2O)_sCF_2CF_2CF_2-$, or their derivatives, wherein p, q, r and s are independently integers so that $M_n$ of $R_f$ is about 150 to 4500; and Z are independently chosen from groups that comprise $-OH$, $-(OH)_2$, $-F$, $-CF_3$, or $-CF_2CF_3$, with the caveat that not all Z are the same.

Also disclosed herein are magnetic stacks that include a substrate; a magnetic layer on the substrate, the magnetic layer configured to store data; a protective overcoat on the magnetic layer; and a lubricant layer on the protective overcoat, the lubricant layer including at least one compound of formula I:

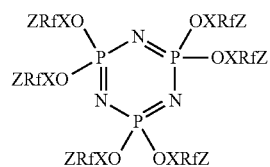

(I)

wherein X are independently $-(CH_2)_b-$, wherein b is 0 or an integer from 1 to 6; $R_f$ are independently $-CF_2O(CF_2CF_2O)_p(CF_2O)_pCF_2-$, $-CF_2CF_2O(CF_2CF_2CF_2O)_rCF_2CF_2-$, $-CF_2CF_2CF_2O(CF_2CF_2CF_2CF_2O)_sCF_2CF_2CF_2-$, or their derivatives, wherein p, q, r, and s are independently integers so that $M_n$ of $R_f$ is about 150 to 4500; and Z are independently chosen from $-CH_2OH$, $-CH_2CH_2OH$, $-CH_2CH_2CH_2OH$, $-CH(OH)CH_2OH$, $-CH_2CH(OH)CH_2OH$, $-CH(CH_2OH)CH_2OH$, $-CH_2OCH_2CH_2OH$, $-CH_2OCH_2CH(OH)CH_2OH$, $-CH_2OCH(CH_2OH)CH_2OH$, $-CH_2OCH_2CH_2OCH_2CH_2OH$, $-F$, $-CF_3$, $-CF_2CF_3$, $-OCF_3$, and $-OCF_2CF_3$.

Also disclosed herein are compounds of formula I

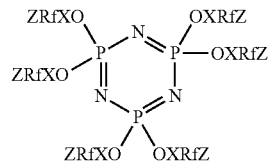

(I)

wherein X are independently $-(CH_2)_b-$, wherein b is 0 or an integer from 1 to 6; $R_f$ are independently $-CF_2O(CF_2CF_2O)_p(CF_2O)_qCF_2-$, $-CF_2CF_2O(CF_2CF_2CF_2O)_rCF_2CF_2-$, $-CF_2CF_2CF_2O(CF_2CF_2CF_2CF_2O)_sCF_2CF_2CF_2-$, or their derivatives, wherein p, q, r and s are independently integers so that $M_n$ of $R_f$ is about 150 to 4500; and Z independently comprise end groups that provide properties selected from enhancing reliability and increase thermal stability of the compound, with the caveat that not all Z are the same.

BRIEF DESCRIPTION OF THE FIGURES

FIG. 1 illustrates a cross section of a magnetic recording media disclosed herein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

"Include," "including," or like terms means encompassing but not limited to, that is, including and not exclusive. It should be noted that "top" and "bottom" (or other terms like "upper" and "lower") are utilized strictly for relative descriptions and do not imply any overall orientation of the article in which the described element is located.

Disclosed herein are compounds for use as lubricants and magnetic stacks such as magnetic recording media containing such lubricants. Disclosed compounds can generally include a cyclotriphosphazene ring having six perfluoropolyether arms with at least one of the end groups on the PFPE arms being different. As used herein, the term cyclotriphosphazene ring refers to a cyclic group that includes three phosphorus and three nitrogen atoms connected in an alternating fashion. As used herein, the term perfluoropolyether refers to a group that has more than one ether group (an ether group is oxygen connected to two alkyl or aryl groups, e.g., 'R—O—R') and a perfluoro group (a perfluoro group generally has all of the hydrogen atoms not contained in functional groups replaced by fluorine atoms).

Exemplary compounds disclosed herein includes compounds of formula I:

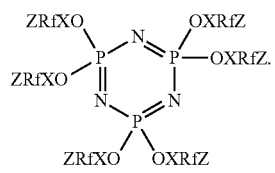

(I)

In formula I, X can, if present independently represent alkyls. In embodiments, X can independently be chosen from $-(CH_2)_b-$, where b can be 0 or an integer from 1 to 6. If b is 0, then X is not present; and if b is from 1 to 6, X is present and represents the respective alkyl.

In formula I, $R_f$ can generally represent perfluoropolyether groups. In embodiments, $R_f$ can independently be chosen from $-CF_2O(CF_2CF_2O)_p(CF_2O)_qCF_2-$, $-CF_2CF_2O(CF_2CF_2CF_2O)_rCF_2CF_2-$, $-CF_2CF_2O(CF_2CF_2CF_2CF_2O)_sCF_2CF_2CF_2-$, or their derivatives, wherein p, q, r and are independently chosen integers. In embodiments, p, q, r, and s are independently integers from 1 to 30; and in embodiments, p, q, r and s are independently integers from 3 to 15. In embodiments, p, q, and r are chosen so that the number average molecular weight ($M_n$) of the $R_f$ group is 150 to 4500; and in embodiments, p, q, r and s are chosen so that Mn of the $R_f$ group is 400 to 2500. In embodiments where $R_f$ includes $-CF_2O(CF_2CF_2O)_p(CF_2O)_qCF_2-$, the ratio of p to q (p/q) can be from about 0.8 to about 1.2. In embodiments, $R_f$ groups such as $CF_2O(CF_2CF_2O)_p(CF_2O)_qCF_2-$ can be derived from Fomblin® Z (Solvay Solexis, Inc. Thorofare, N.J.); and $R_f$ groups such as $-CF_2CF_2O(CF_2CF_2CF_2O)_rCF_2CF_2-$ can be derived from Demnum® (Daikin America, Inc. Orangeburg, N.Y.) for example.

In formula I, Z can generally represent functional groups. Z can also be referred to as end groups. In embodiments, Z can independently be chosen from groups that include hydroxyl groups, esters groups, aldehyde groups, fluorine, fluorocarbon groups, aromatic groups, piperonyl groups, and derivatives thereof for example. In embodiments, Z can independently be chosen from groups that include $-OH$, $-(OH)_2$, $-COOCH_3$, F, $-CF_3$, $-CF_2CF_3$, $-C_6H_5$, piperonyl

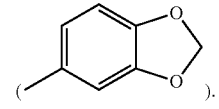

A group that includes $-(OH)_2$ refers to a group that includes two hydroxyl groups, whether on a single carbon or different carbons. In embodiments, Z can independently be chosen from groups that include $-OH$, $-(OH)_2$, and $-CF_3$. In embodiments, Z can independently be chosen from $-CH_2OH$, $-OCH_2CH_2OH$, $-CH_2CH_2OH$, $-CH_2CH_2CH_2OH$, $-CH(OH)CH_2OH$, $-CH_2CH(OH)CH_2OH$, $-CH(CH_2OH)CH_2OH$, $-CH_2OCH_2CH(OH)CH_2OH$, $-CH_2OCH(CH_2OH)CH_2OH$, $-CH_2OCH_2CH_2OCH_2CH_2OH$, F, $-CF_3$, $-CF_2CF_3$, $-C_6H_5$, and piperonyl

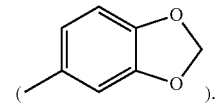

In embodiments, Z can independently be chosen from $-CH_2OH$, $-CH(OH)CH_2OH$, and $-CF_3$.

In formula I, not all Z groups can be the same, or stated another way, in formula I, at least one Z group must be different than the other Z groups. In embodiments, at least two Z groups are different than the other Z groups (the other four Z groups); and in embodiments, three Z groups are the same and the other three Z groups are the same, but different than the first three Z groups. In embodiments, a compound of formula I can include two different Z groups, three different Z groups, four different Z groups, five different Z groups, or six different Z groups. In embodiments a compound of formula I can include two different Z groups.

An exemplary compound according to formula I includes three Z groups that are $-CH_2OH$ and three Z groups that are $-CF_3$. An exemplary structure of such a compound can be seen in formula II below:

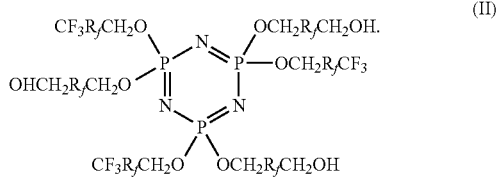

(II)

It should be noted in formula II, that the end groups need not be alternately positioned, as they are seen in formula II, they can be positioned in any configuration on the three phosphorous (P) atoms.

Another exemplary compound according to formula I includes three Z groups that are —$CH_2OH$ and three Z groups that are —$CH(OH)CH_2OH$. An exemplary structure of such a compound can be seen in formula III below:

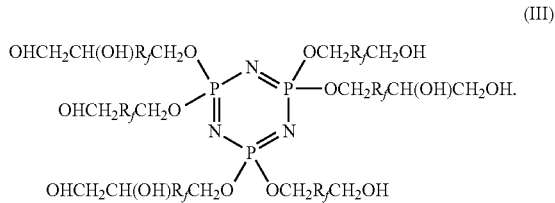

(III)

It should be noted in formula III, that the end groups need not be alternately positioned, as they are seen in formula III, they can be positioned in any configuration on the three phosphorous (P) atoms.

Another exemplary compound according to formula I includes two Z groups that are —$CF_3$, two Z groups that are —$CH_2OH$ and two Z groups that are —$CH(OH)CH_2OH$. An exemplary structure of such a compound can be seen in formula IV below:

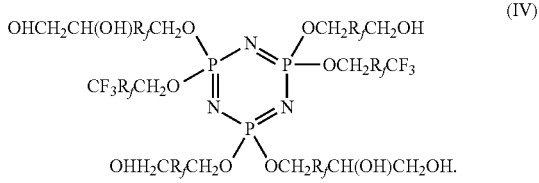

(IV)

It should be noted in formula IV, that the end groups need not be alternately positioned, as they are seen in formula IV, they can be positioned in any configuration on the three phosphorous (P) atoms.

Compounds of formula I-IV can be synthesized by reacting a trifluoromethylphenoxyl substituted cyclophosphazene and a mixture of perfluoropolyethers having one hydroxyl group at one end and a different groups at the other ends. As an example, the compound of formula II can be obtained by the following synthesis method. 100 g of trifluoromethylphenoxyl substituted cyclophosphazene was dissolved in the solvent ditrifluoromethylbenzene (~500 g). Then 300 g of a perfluoropolyether (~1500 in Mn) having one hydroxyl group at both ends; 300 g of a perfluoropolyether (~1500 in Mn) having one hydroxyl group at one terminal and a —$CF_3$ at the other terminal; and 18 g of metallic sodium were added to the solution. The reaction mixture was agitated at about 70° C. for about 25 hours. The resulting mixture was first washed with water followed by subsequent purification by means of column chromatography, yielding ~50 g of the desired Compound II.

Compounds disclosed herein can be utilized as lubricants or in lubricant compositions. When utilized as a portion of a lubricant composition, other components may be combined with the compound (or compounds) of formula I. Such lubricants can be utilized in magnetic stacks such as magnetic recording media. FIG. 1 depicts a cross section of an exemplary magnetic recording media. The exemplary magnetic recording media or disc 100 can include a substrate 105; a magnetic layer 110 on the substrate, the magnetic layer configured to store data (generally in the form of "0" or "1"); a protective overcoat 115 on the magnetic layer; and a lubricant layer 120 on the protective overcoat. Discs can also include other layers not depicted herein, such as for example underlayers, adhesion layers, etc. Discs, as disclosed herein can be textured or can include various portions, such as a data zone (the portion of the disc configured to store information) and a landing zone (the portion of the disc where the slider that holds the read/write head rests while the disc is not in use and takes off from when the disc drive is started up). Lubricants as disclosed herein can be utilized differently or the same in various portions of discs.

Disclosed compounds or lubricant compositions containing disclosed compounds can be deposited by various means, including for example dip coating, spin-on coating, vapor deposition and/or electrospray.

Compounds disclosed herein can be utilized in the lubricant layer 120. The lubricant layer 120 can function to minimize, reduce or eliminate wear, friction, and stiction between the disc and the read/write head as the read/write head passes over the disc. Generally, the lubricant layer can have a thickness from 3 Å to 30 Å, from 5 Å to 20 Å, or from 8 Å to 15 Å. The lubricant layer can be either partially bonded to the underlying carbon overcoat or fully bonded.

Compounds disclosed herein can provide various properties as lubricants or in lubricant compositions. Various portions of compounds of formula I can provide different properties. As discussed above, compounds of formula I disclosed herein include at least two different end groups (the Z in formula I). The use of at least two different end groups enables the properties of the compound to be more precisely formulated. Various properties can be considered, including for example polarity, viscosity, affinity to underlying carbon overcoat and mobility.

Compounds of formula I include a cyclotriphosphazene core ($N_3P_3$). Phosphazene functions as a Lewis base, which when utilized as a lubricant, can improve chemical and/or thermal stability when the lubricant is brought into contact with a Lewis acid like $Al_2O_3$ or MgO. The phosphazene portion of a compound of formula I also functions to provide the compound with six different arms (in this case PFPEs with end groups), which can be thought of or referred to as a star shaped molecule. Star shaped structures can provide a smaller radius of gyration when compared to linear molecules of the same molecular weight. This can provide a lubricant layer that has a relatively low profile conformation. As used herein, the "profile" refers to a particular type of conformation of lubricant molecules within a thin film. A low profile means a "flat" conformation of lubricant film and tends to provide a smoother lubricant surface. A low profile can be advantageous because it can afford lower head to media spacing (HMS) and minimize or eliminate transfer of the lubricant molecules to the read/write head. For example, clearances as small as 3 to 5 Å can be utilized, which can afford reduction in HMS. The overall shape of the compound (a central core with PFPE arms having functional end groups) can also generally lead to neighboring molecules being relatively closely packed when deposited. This can enable relatively strong bonding to the carbon overcoat.

The particular end groups (Z in formula I) can be chosen because of the properties they provide. For example, end groups that include a single hydroxyl (—OH) group can enhance reliability of a lubricant because it can provide an appropriate affinity and mobility to the carbon surface. Polymer arms with end groups that include fluoroalkyls (such as —CF$_3$ and CF$_2$CF$_3$ for example) tend to increase the molecular weight of the compound which minimizes evaporation which can increase the thermal stability of the lubricant. End groups that include two hydroxyls ((OH)$_2$) can provide strong affinity to the carbon overcoat which can reduce lube transfer from the media to the head. A good combination of different end groups in a single molecule can enable the desired and balanced reliability of the head-disk interface without losing or detrimentally affecting any single property.

Additional exemplary compounds are those of formula I

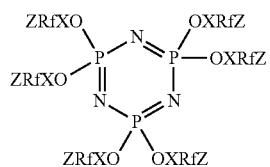

(I)

wherein X are independently —(CH$_2$)$_b$—, wherein b is 0 or an integer from 1 to 6; R$_f$ are independently —CF$_2$O(CF$_2$CF$_2$O)$_p$(CF$_2$O)$_q$CF$_2$—, —CF$_2$CF$_2$O(CF$_2$CF$_2$CF$_2$O)$_r$CF$_2$CF$_2$—, —CF$_2$CF$_2$CF$_2$O(CF$_2$CF$_2$CF$_2$CF$_2$O)$_s$CF$_2$CF$_2$CF$_2$—, or their derivatives, wherein p, q, r and s are independently integers so that M$_n$ of R$_f$ is about 150 to 4500; and Z independently comprise end groups that provide properties selected from enhancing reliability and increase thermal stability of the compound, with the caveat that not all Z are the same.

In such embodiments, exemplary Z groups that can enhance reliability can include —CH$_2$OH, —OCH$_2$CH$_2$OH, —CH$_2$CH$_2$OH, —CH$_2$CH$_2$CH$_2$OH, —CH(OH)CH$_2$OH, —CH$_2$CH(OH)CH$_2$OH, —CH(CH$_2$OH)CH$_2$OH, —CH$_2$OCH$_2$CH(OH)CH$_2$OH, —CH$_2$OCH(CH$_2$OH)CH$_2$OH, and —CH$_2$OCH$_2$CH$_2$OCH$_2$CH$_2$OH for example. Exemplary Z groups that can increase thermal stability can include F, —CF$_3$, and —CF$_2$CF$_3$ for example.

What is claimed is:
1. A compound of formula I:

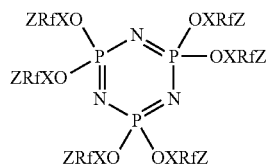

(I)

wherein X are independently —(CH$_2$)$_b$—, wherein b is 0 or an integer from 1 to 6;
R$_f$ are independently —CF$_2$O(CF$_2$CF$_2$O)$_p$(CF$_2$O)$_q$CF$_2$—, —CF$_2$CF$_2$O(CF$_2$CF$_2$CF$_2$O)$_r$CF$_2$CF$_2$—, or —CF$_2$CF$_2$CF$_2$O(CF$_2$CF$_2$CF$_2$CF$_2$O)$_s$CF$_2$CF$_2$CF$_2$, wherein p, q, r, and s are independently integers so that M$_n$ of R$_f$ is about 150 to 4500; and
Z are independently chosen from:
—CH$_2$OH, —CH$_2$CH$_2$OH, —CH$_2$CH$_2$CH$_2$OH, —CH(OH)CH$_2$OH, —CH$_2$CH(OH)CH$_2$OH, —CH$_2$OCH$_2$CH(OH)CH$_2$OH, —CH$_2$OCH(CH$_2$OH)CH$_2$OH, —CH$_2$OCH$_2$CH$_2$OCH$_2$CH$_2$OH, —F, —CF$_3$, —CF$_2$CF$_3$, —OCH$_2$CH$_2$OH, —CH(CH$_2$OH)CH$_2$OH, —C$_6$H$_5$, and piperonyl with the caveat that not all Z are the same.

2. The compound according to claim 1, wherein at least one Z is different than the other five Z.

3. The compound according to claim 1, wherein three Z are the same and the other three Z are the same.

4. The compound according to claim 1, wherein three Z are —CH$_2$OH and three Z are —CF$_3$.

5. The compound according to claim 1, wherein three Z are —CH$_2$OH and three Z are —CH(OH)CH$_2$OH.

6. The compound according to claim 1, wherein two Z are —CH$_2$OH, two Z are —CH(OH)CH$_2$OH, and two Z are —CF$_3$.

7. The compound according to claim 1, wherein each R$_f$ independently have a M$_n$ from about 400 to about 2500.

8. A magnetic stack comprising:
a substrate;
a magnetic layer on the substrate;
a protective overcoat on the magnetic layer; and
a lubricant layer on the protective overcoat, the lubricant layer comprising at least one compound of formula I:

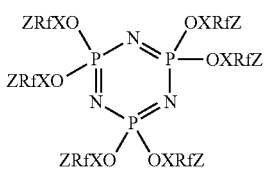

(I)

wherein X are independently —(CH$_2$)$_b$—, wherein b is 0 or an integer from 1 to 6;
R$_f$ are independently —CF$_2$O(CF$_2$CF$_2$O)$_p$(CF$_2$O)$_q$CF$_2$—, —CF$_2$CF$_2$O(CF$_2$CF$_2$CF$_2$O)$_r$CF$_2$CF$_2$—, or —CF$_2$CF$_2$CF$_2$O(CF$_2$CF$_2$CF$_2$CF$_2$O)$_s$CF$_2$CF$_2$CF$_2$,
wherein p, q, r and s are independently integers so that M$_n$ of R$_f$ is about 400 to 2500; and
Z are independently chosen from: —CH$_2$OH, —CH$_2$CH$_2$OH, —CH$_2$CH$_2$CH$_2$OH, —CH(OH)CH$_2$OH, —CH$_2$CH(OH)CH$_2$OH, —CH$_2$OCH(OH)CH$_2$OH, —CH$_2$OCH(CH$_2$OH)CH$_2$OH, —CH$_2$OCH$_2$CH$_2$OCH$_2$CH$_2$OH, —F, —CF$_3$, —CF$_2$CF$_3$, —OCH$_2$CH$_2$OH, —CH(CH$_2$OH)CH$_2$OH, —C$_6$H$_5$, and piperonyl, with the caveat that not all Z are the same.

9. The magnetic stack according to claim 7, wherein the lubricant layer has a thickness from about 3 Å to about 30 Å.

10. The magnetic stack according to claim 8, wherein three Z are —CH$_2$OH and three Z are —CF$_3$.

11. The magnetic stack according to claim 8, wherein three Z are —CH$_2$OH and three Z are —CH(OH)CH$_2$OH.

12. The magnetic stack to claim 8, wherein two Z are —CH$_2$OH, two Z are —CH(OH)CH$_2$OH and two Z are —CF$_3$.

13. A magnetic stack comprising:
a substrate;
a magnetic layer on the substrate, the magnetic layer configured to store data;
a protective overcoat on the magnetic layer; and
a lubricant layer on the protective overcoat, the lubricant layer comprising at least one compound of formula I:

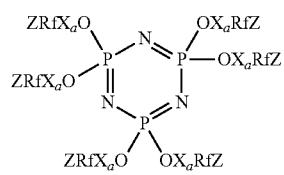
(I)

wherein X are independently —(CH$_2$)$_b$—, wherein b is an integer from 1 to 6;
a are independently 0 or 1;
R$_f$ are independently —CF$_2$O(CF$_2$CF$_2$O)$_p$(CF$_2$)$_q$CF$_2$—, —CF$_2$CF$_2$O(CF$_2$CF$_2$CF$_2$O)$_r$CF$_2$CF$_2$—, or —CF$_2$CF$_2$CF$_2$O(CF$_2$CF$_2$CF$_2$CF$_2$O)$_s$CF$_2$CF$_2$CF$_2$,
wherein p, q, r and s are independently integers from 3 to 15; and
Z are independently chosen from —CH$_2$OH, —CH$_2$CH$_2$OH, —CH$_2$CH$_2$CH$_2$OH, —CH(OH)CH$_2$OH, —CH$_2$CH(OH)CH$_2$OH, —OCH$_2$CH$_2$OH, —CH(CH$_2$OH)CH$_2$OH, —COOCH$_3$, CH$_2$OCH$_2$CH(OH)CH$_2$OH, —CH$_2$OCH(CH$_2$OH)CH$_2$OH, —CH$_2$OCH$_2$CH$_2$OCH$_2$CH$_2$OH, —F, —CF$_3$, and —CF$_2$CF$_3$.

14. The magnetic stack according to claim 13, wherein three Z are —CH$_2$OH and three Z are —CF$_3$.

15. The magnetic stack according to claim 13, wherein three Z are —CH$_2$OH and three Z are —CH(OH)CH$_2$OH.

16. The magnetic stack according to claim 13, wherein two Z are —CH$_2$OH, two Z are —CH(OH)CH$_2$OH and two Z are —CF$_3$.

17. A compound of formula I

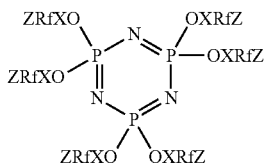
(I)

wherein X are independently —(CH$_2$)$_b$—, wherein b is 0 or an integer from 1 to 6;
R$_f$ are independently —CF$_2$O(CF$_2$CF$_2$O)$_p$(CF$_2$O)$_p$CF$_2$—, —CF$_2$CF$_2$O(CF$_2$CF$_2$CF$_2$O)$_r$CF$_2$CF$_2$—, or —CF$_2$CF$_2$CF$_2$O(CF$_2$CF$_2$CF$_2$CF$_2$O)$_s$CF$_2$CF$_2$CF$_2$,
wherein p, q, r and s are independently integers so that M$_n$ of R$_f$ is about 150 to 4500; and
Z are independently selected from —CH$_2$OH, CF$_3$ and CH(OH)CH$_2$OH.

* * * * *